(12) United States Patent
Read et al.

(10) Patent No.: US 7,803,594 B2
(45) Date of Patent: Sep. 28, 2010

(54) **TYPE III *T. BRUCEI* ARGININE METHYLTRANSFERASE**

(75) Inventors: Laurie K. Read, Orchard Park, NY (US); John Fisk, Amherst, NY (US)

(73) Assignee: University of Buffalo, Office of Science & Tech Transfer, Amherst, NY (US)

( * ) Notice: Subject to any disclaimer, the term of this patent is extended or adjusted under 35 U.S.C. 154(b) by 0 days.

(21) Appl. No.: 12/536,870

(22) Filed: Aug. 6, 2009

(65) Prior Publication Data

US 2010/0047893 A1 Feb. 25, 2010

(51) Int. Cl.
 *C12N 9/10* (2006.01)
 *C12N 1/00* (2006.01)
 *C12N 1/20* (2006.01)
 *C12N 15/00* (2006.01)
 *C07H 21/04* (2006.01)

(52) U.S. Cl. ............... 435/193; 435/252.3; 435/320.1; 435/243; 536/23.2

(58) Field of Classification Search ............... 435/193, 435/243, 252.3, 320.1; 536/23.2
See application file for complete search history.

(56) References Cited

OTHER PUBLICATIONS

Fisk et al. Journal of Biological Chemistry, 284: 11590-11600 (2009).*

* cited by examiner

*Primary Examiner*—Tekchand Saidha
(74) *Attorney, Agent, or Firm*—Medlen & Carroll, LLP

(57) ABSTRACT

The invention relates to enzymes in *Trypanosoma brucei*, and in particular, protein arginine methyltransferases. A unique, highly active recombinant arginine methyltransferase capable of monomethylation of peptides and proteins is described.

6 Claims, 21 Drawing Sheets

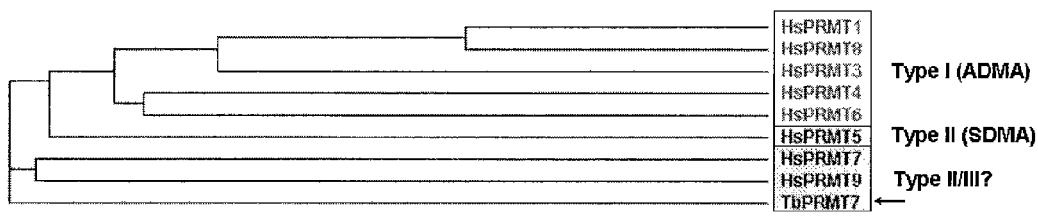

B

C

| | | |
|---|---|---|
| HsPRMT7N | VLDIGTGTGLLS | |
| DmDart7N | VLDIGTGTGLLS | Motif I |
| TbPRMT7 | VLEIGAGSGLLS | |

| | | |
|---|---|---|
| HsPRMT7N | CYAIE | |
| DmDart7N | VTACE | Post I |
| TbPRMT7 | VVAVE | |

| | | |
|---|---|---|
| HsPRMT7N | EGDMPCRANILVTELFDTELIGEGAL | |
| DmDart7N | E-DMPRRANILVAELLDTELIGEGAL | Motif II and Double E loop |
| TbPRMT7 | K-HPEPPDVLISETEGTMMLGESAL | |

| | | |
|---|---|---|
| HsPRMT7N | RLVEENCEAVP | |
| DmDart7N | ELLTEDALCIP | Motif III |
| TbPRMT7 | RLLKPTTKIIP | |

| | | |
|---|---|---|
| HsPRMT7N | DH-WMQ | |
| DmDart7N | DH-WMQ | "THW" Loop |
| TbPRMT7 | DMQWGQ | |

FIGURE 9

The DNA coding sequence (SEQ ID NO: 6) for the methyltransferase of the present invention.

```
ATGCCCCCAA AGCAGCACCG CCACCAAAAG AAGGACAAGA ACGACAATGC GTTGCAGAAC
ACAATTGGGT TTGTTCCTCC TGGAGCCACT CTCGCTAGTG TGTCCGGTTA CCGTCCTCCT
GACGCCTTTG TTAACCGAAT CGATAGAAAT ATACCGGTCC CCGCCCGCCT GCGCCACACA
CCAGTTTCCC TCATTGAAGC GGTGAATGAT TTCCACTACG CAATGATGAA TGATGAGGAA
CGCAATAATT TCTACTATGA GGTTTTGAAG AAACATGTGA CTCCAGAAAC TGGTGTACTG
GAGATTGGTG CTGGATCAGG TTTACTGTCT CTCATGGCCG CTAAGCTTGG TGCGAAGTGG
GTTGTTGCAG TGGAGGGAAG CGAAGAATTG GCGAAGTTGG CACGTGAGAA CATCCGTGCT
AATAATATGG AACATCAGGT AAAGGTTCTT CATATGATGA GTACAGAGCT CAAATCAAAG
CACTTACCCG AACCACCGGA TGTTCTTTTG TCGGAGATAT TTGGAACGAT GATGCTTGGA
GAGTCGGCAC TAGATTATGT TGTGGATGTG AGAAATAGGT TACTGAAGCC AACAACGAAA
ATAATTCCAC AGTTTGGAAC GCAATACGCC GTCCCCATCG AGTGCGACGC TCTTCACCGT
ATTTCATCTG TATCGGGCTG GCGTGACTTG GACCTGAAGC ATATGATGAC ATTGCAGGAT
ACCGTGAGTA TTGTCTTTGC TAAACACTAC GGTATCCGTA TGAACAGTGT GAACTTCAGG
AGGTTAAGCG ATCCCATAGA GCTATTCAGA GTCGACTTTA GCTCCTCGAA TCGGAACGAT
ATTCCTCGGC GAAAGCACTT CGACGTTGTG GCTAAAGAGA GTGGAACGGC CCATGCAATG
TTGTTCTACT GGAAAGTTAC CGACGATGAA TTTGTCATGT CAACGGACCC GGAAGACACA
GTCAACAACT TCCCACGTGA TATGCAGTGG GGTCAGGCGC TTCAGCTGTT GGACGCCTCT
AACGGCCCTC TGCCCACACC GGTTGTATTC ACCGAGGGAA AGAATTATAA CTTTGAGTGT
AATTTTTCGG GAGACCGCGT GATTCTTCAC ATGCAGCTCT GCCCCGAAAG TGGGAACGGT
GAAATGACTG AGTGCGAGGG CAAAACAACC TGA
```

FIGURE 10
A
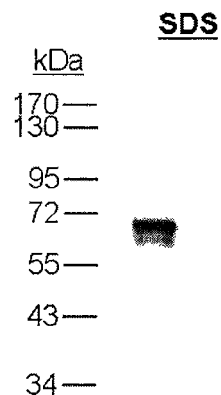
B
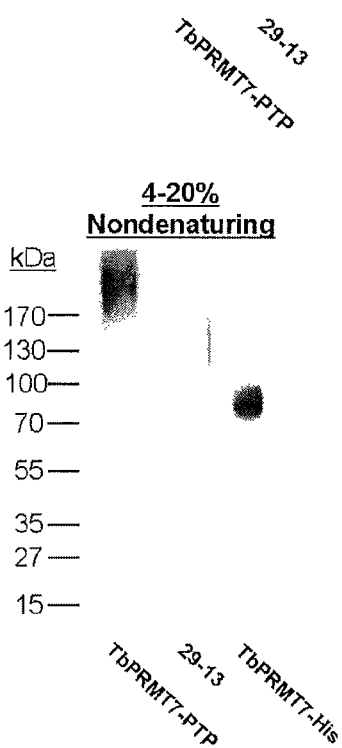
C
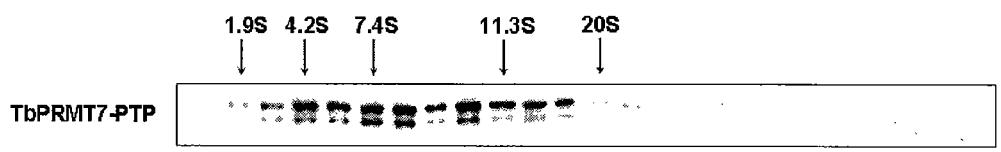

us 7,803,594 B2

TYPE III *T. BRUCEI* ARGININE METHYLTRANSFERASE

This invention was supported by grant number RO1 AI60260 from the National Institutes of Health. The Government has certain rights in the invention.

FIELD OF THE INVENTION

The invention relates to enzymes in *Trypanosoma brucei*, and in particular, protein arginine methyltransferases.

BACKGROUND OF THE INVENTION

Post-translation modification of proteins is one of several mechanisms that organisms use to for purposes of regulating cellular functions. There are several types of protein modifications that may occur. Different types of modifications to one particular protein can direct different activities of that protein. One form of protein modification is that of methylation which adds a methyl ($CH_3$ group). An enzyme that catalyzes transfer of methyl group is a methyltransferase. One class of methyltransferase that mediates methylation to the amino acid arginine is that of the protein arginine methyltransferase (PRMTs). Arginine methylation is involved in regulating RNA processing, signal transduction, DNA repair and transcription (DNA→RNA). The group that is submitting this disclosure is working to identify and characterize PRMTs class members as part of their ongoing work. Within the PRMT class there are subclasses: Type I asymmetrically dimethylates; Type II symmetrically dimethylates; and Type I mono-methylates at arginine amino acids.

SUMMARY OF THE INVENTION

This disclosure provides a new member of the PRMT Type III class, PRMT7, from the parasite *Trypanosoma brucei*. Recombinant protein has been successfully prepared. The protein disclosed herein methylates at a rate at least 100× higher than Type I and Type II enzymes, and monomethylates a wide range of substrates. PRMT7 can be used as research tool to test the effect on monomethylation on a protein's activity, protein-protein interactions, and/or protein nucleic acid interactions. In addition, production of the enzyme in heterologous mammalian expression systems may prove useful in determining the role of monomethylarginine modification in mammalian cells The enzyme disclosed herein catalyzes monomethylation of selected arginine residues in many proteins. It will be useful when purified from bacterial expression systems for in vitro experiments designed to test the effect on monomethylation on a protein's activity, protein-protein interactions, and/or protein nucleic acid interactions. In addition, production of the enzyme in heterologous mammalian expression systems may prove useful in determining the role of monomethylarginine modification in mammalian cells.

In summary, this highly active recombinant arginine methyltransferase is capable of monomethylation of peptides and proteins. The enzyme is the most active recombinant Type III protein arginine methyltransferase described to date.

In one embodiment, the present invention contemplates a purified and/or isolated methyltransferase having the amino acid sequence of SEQ ID NO: 5, including where it is mixed with substrate. In one embodiment, the present invention contemplates the methyltransferase as a dimer. Also contemplated is the nucleic acid sequence (SEQ ID NO:6) coding for the methyltransferase, including but not limited to where the coding sequence is in a vector (and e.g. where the vector is in a host cell). In one embodiment, the coding sequence is operably linked to a heterologous promoter. The present invention is not limited by the nature of the heterologous promoter employed; in a preferred embodiment, the heterologous promoter is an inducible promoter (the promoter chosen will depend upon the host cell chosen for expression as is known in the art). The invention is not limited by the nature of the inducible promoter employed.

The present invention also contemplates primers that can amplify the coding sequence, as well as oligonucleotides which can hybridize to the coding sequence, or portion thereof.

In one embodiment, the present invention contemplates using the enzyme to screen for substrates of the enzyme. In a further embodiment, the invention contemplates screening a library of peptides to identify potential substrates.

In one embodiment, the present invention contemplates using the enzyme in an assay for determining methylation based upon measuring the decreasing concentration of the cofactor S-adenosylmethionine (AdoMet/SAM).

In one embodiment, the present invention contemplates using a "FLAG-tagged" recombinant version of the enzyme to isolate methylation substrates of the enzyme. In one embodiment, isolation of the substrates contemplates using an "anti-FLAG" antibody to isolate the "FLAG-tagged" recombinant version of the enzyme and the associated substrate.

DESCRIPTION OF THE FIGURES

FIG. 2 is characterization of TbPRMT7. A. CLUSTALW derived cladogram of TbPRMT7 compared with the seven known active human PRMTs as well as the uncharacterized PRMT9(4q31) protein. The human PRMTs are grouped as known Type I PRMTs (ADMA catalyzing), Type II (SDMA catalyzing), and the either Type II or III catalyzing PRMT7. The position of TbPRMT7 is indicated by the arrow. B. Alignment of TbPRMT7 with full-length human PRMT7 (structure adapted from Bedford, M. T. (2007) Arginine methylation at a glance, Journal of Cell Science 120, 4243-4246.). The homology of TbPRMT7 with the N-terminal PRMT enzymatic motifs of HsPRMT7 is shown above the aligned proteins. C. CLUSTALW alignment and Boxshade of TbPRMT7 with the N-terminal motifs of HsPRMT7.

(BF). Depletion of TbPRMT7 mRNA was confirmed using qRT-PCR (PF) or northern blotting (BF).

Figure 1:
FIG. 1 is a comparison of TbPRMT7 (390 amino acids) to its closes human homolog (Hs PRMT7; 692 amino acids). TbPRMT7 (390 amino acids) has a significantly truncated structure compared to its closes human homolog (Hs PRMT7; 692 amino acids). Vertical bars indicate conserved AdoMet binding domain, which is duplicated in HsPRMT7, but not in TbPRMT7.
Figure 3:
FIG. 3 is a comparison of Human PRMT7 (HsPRMT7), *T. brucei* PRMT7 (TbPRMT7), and Human PRMT9 (HsPRMT9), demonstrating that the PRMT7 homologue in *T. brucei* is shorter than other PRMT7.
Figure 4A:
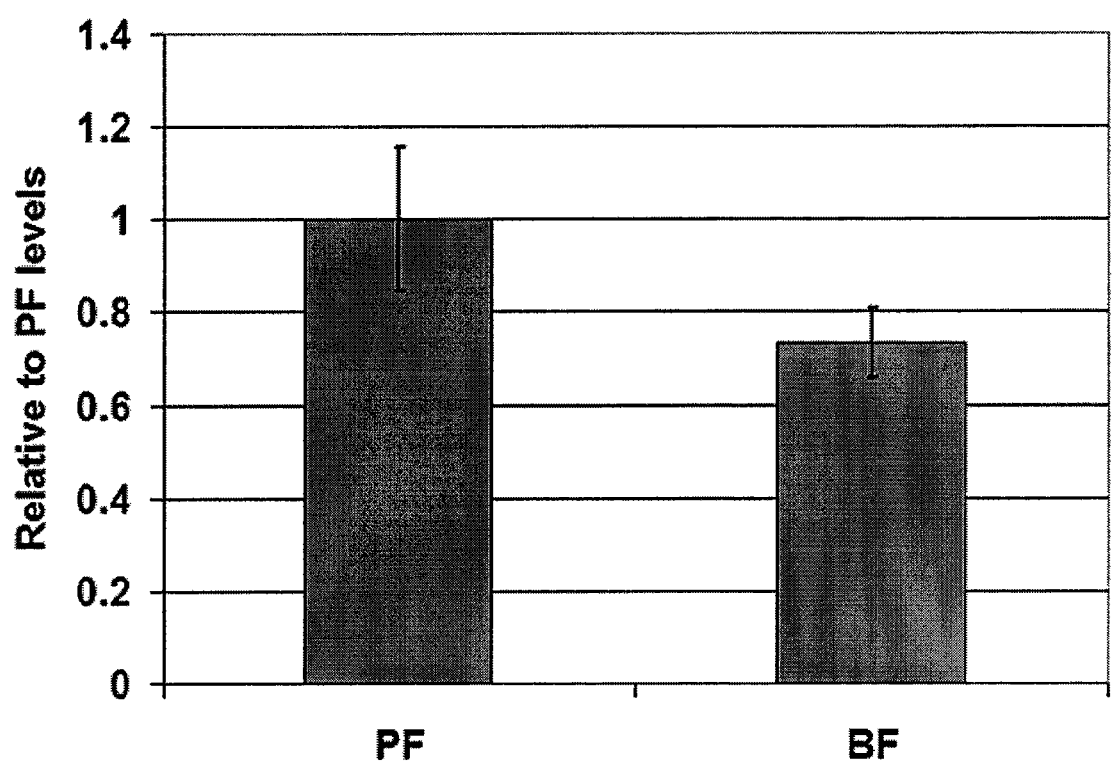
FIG. 4 shows TbPRMT7 is expressed in two life cycle stages and its depletion does not affect growth. A, qRT-PCR analysis of the relative amounts of TbPRMT7 mRNA in procyclic (PF) and bloodstream (BF) form *T. brucei*. TbPRMT7 levels were normalized to β-tubulin and RNA levels in PF were set to one. B, Clonal procyclic (upper) and bloodstream (lower) form *T. brucei* cells lines expressing tetracycline-regulated TbPRMT7 RNAi were established. Production of dsRNA was induced using 2.5 μg/mL tetracycline on Day 0, and total cells were counted thereafter until day 10 (PF) or 12
Figure 4B:
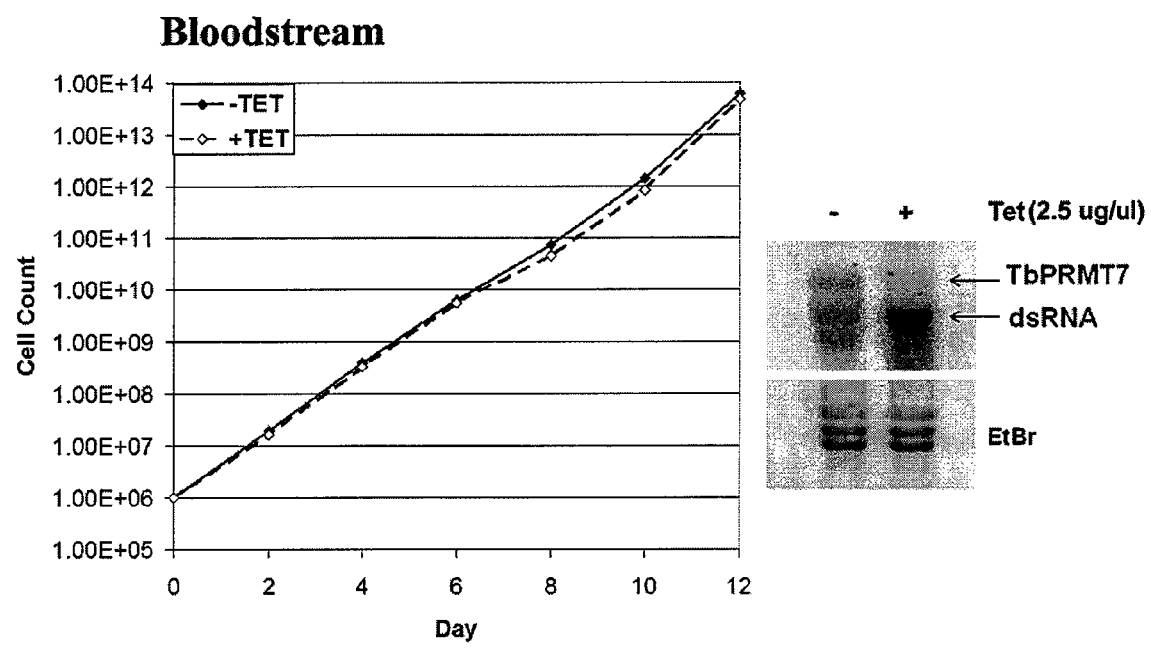
Figure 4B:
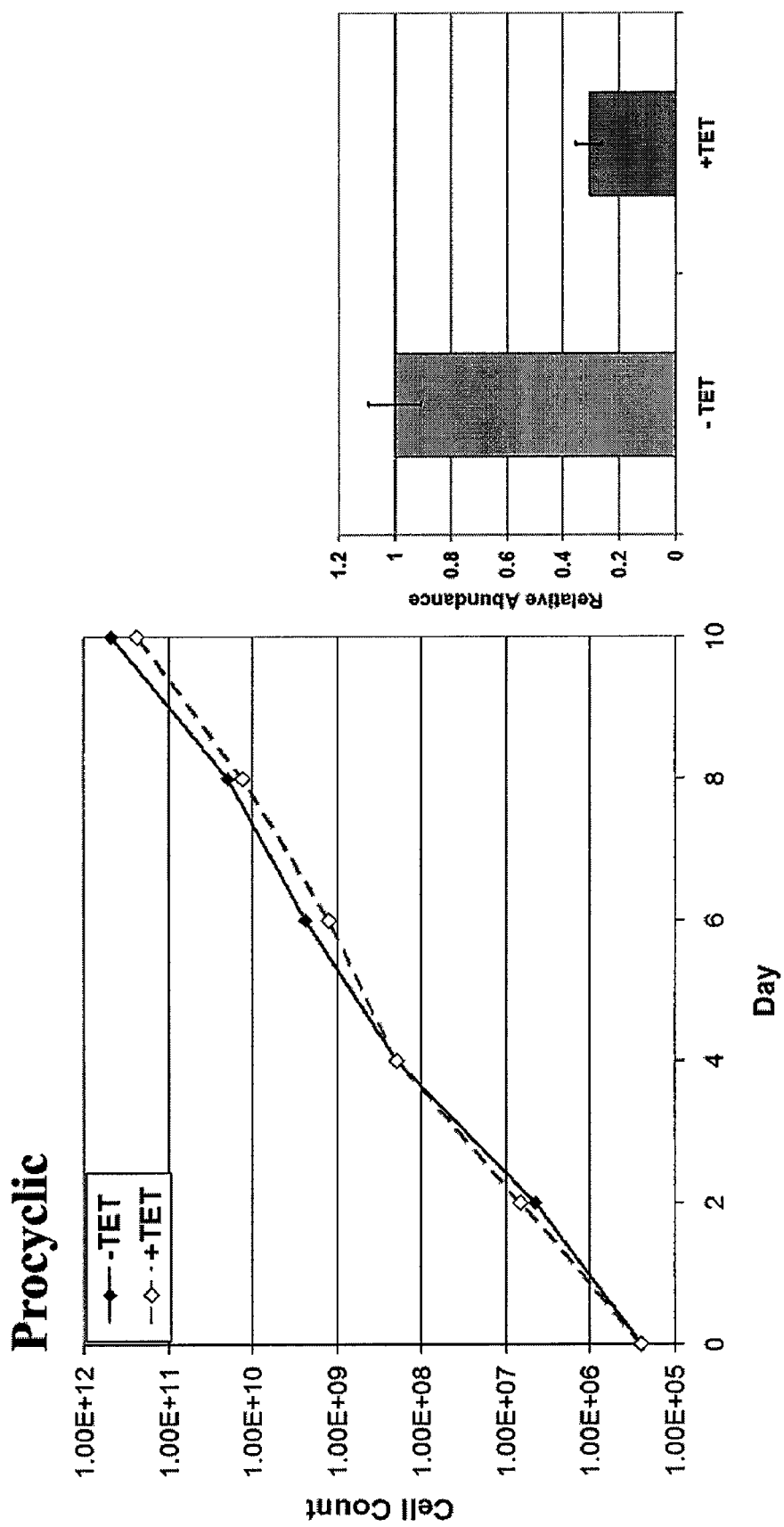
Figure 5:
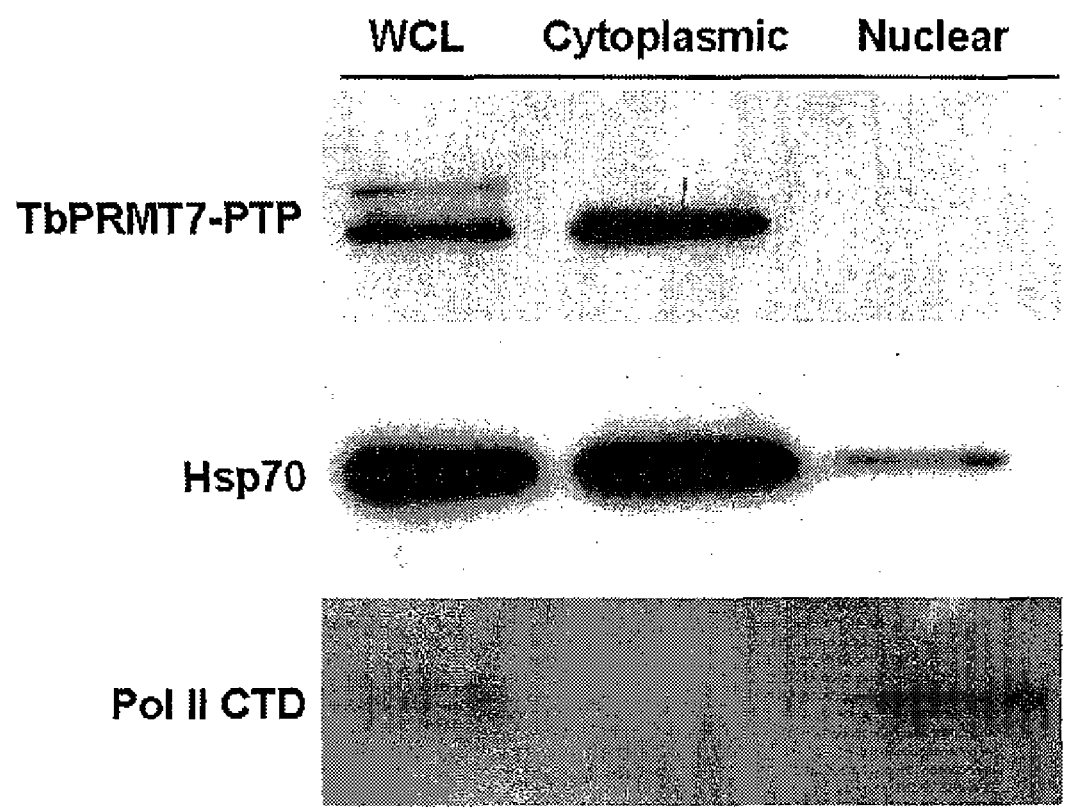
Figure 6A:
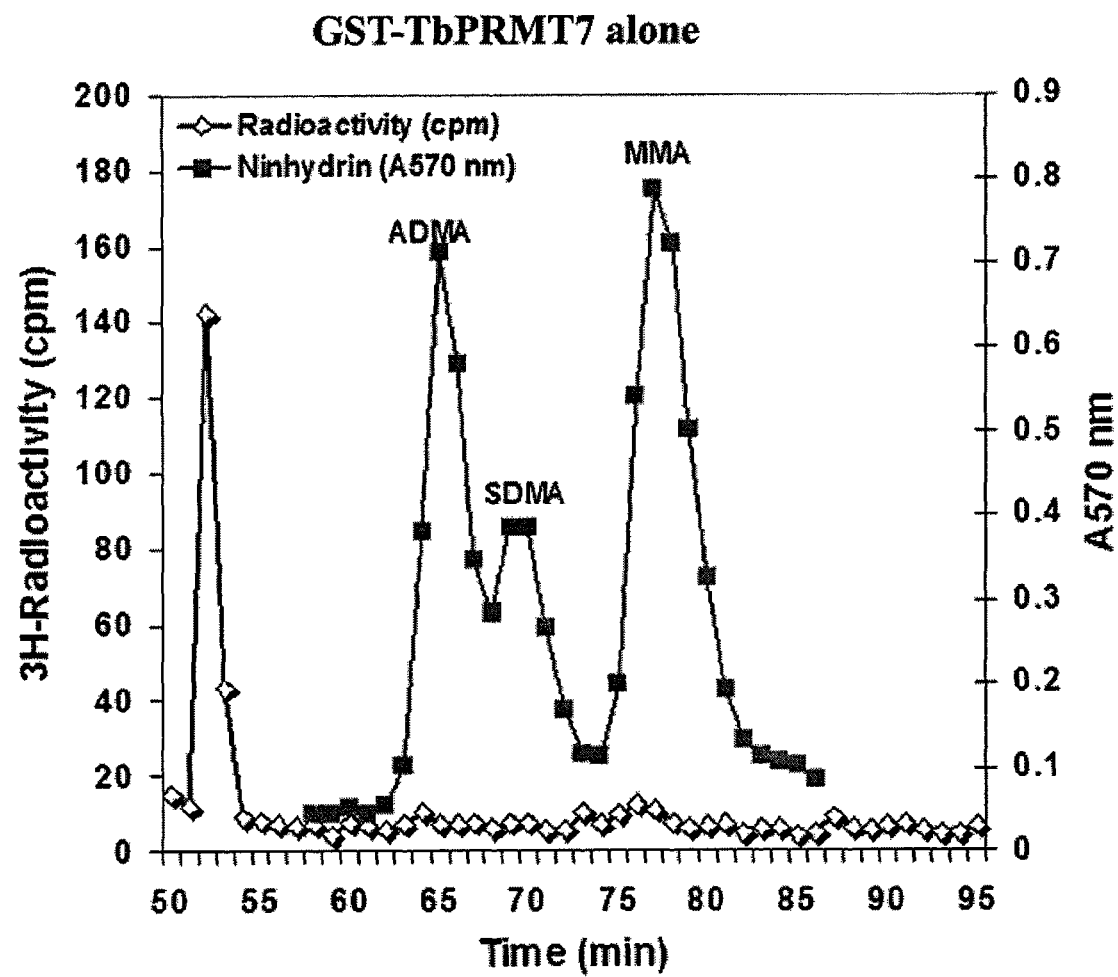
Figure 6B:
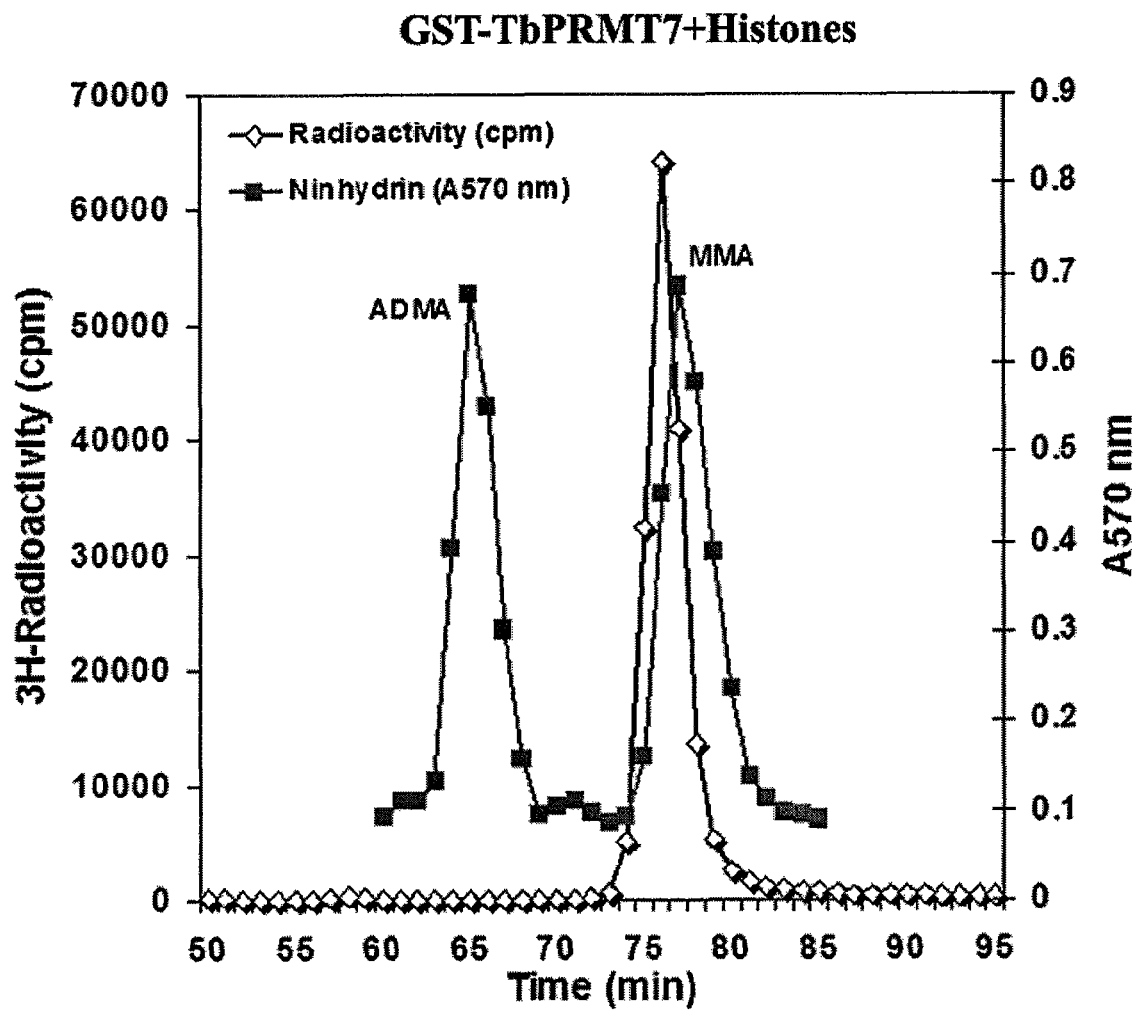
Figure 6C:
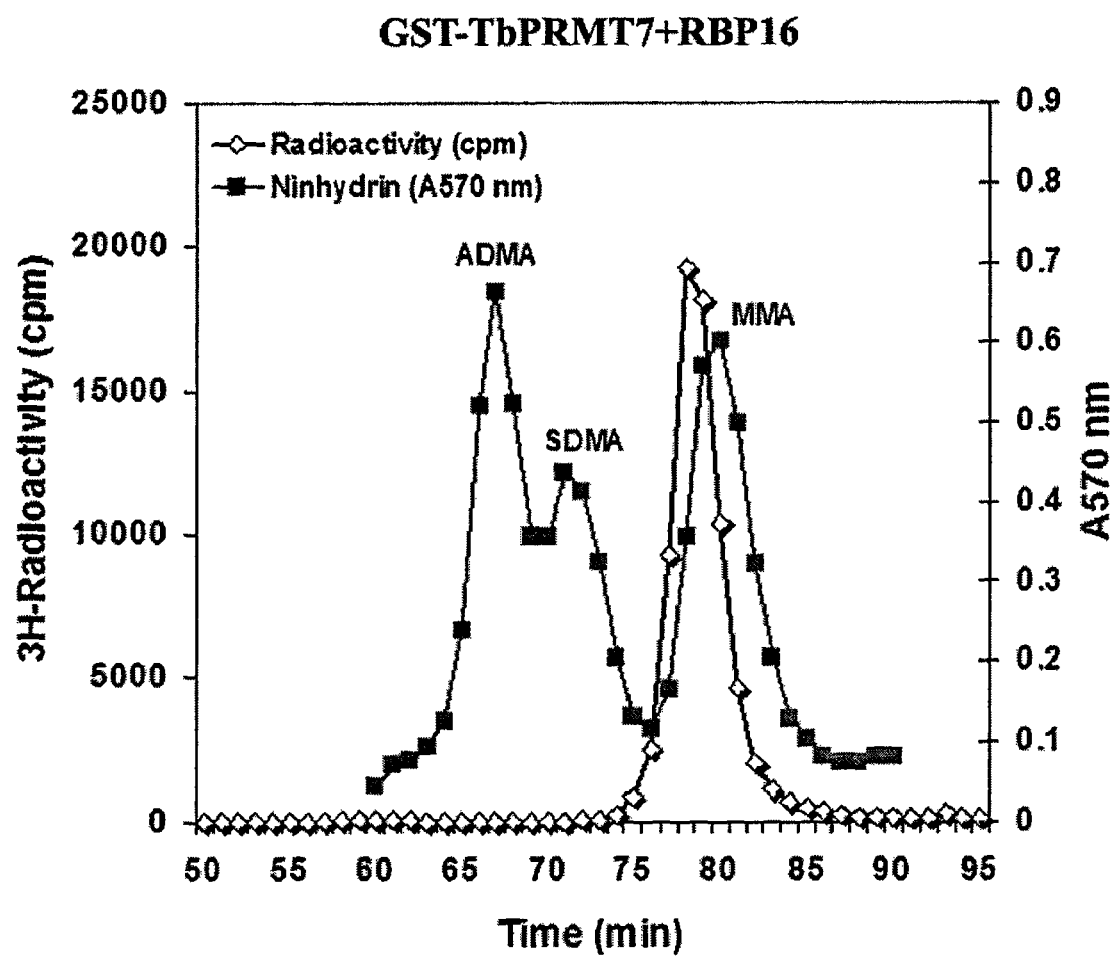
Figure 6D:
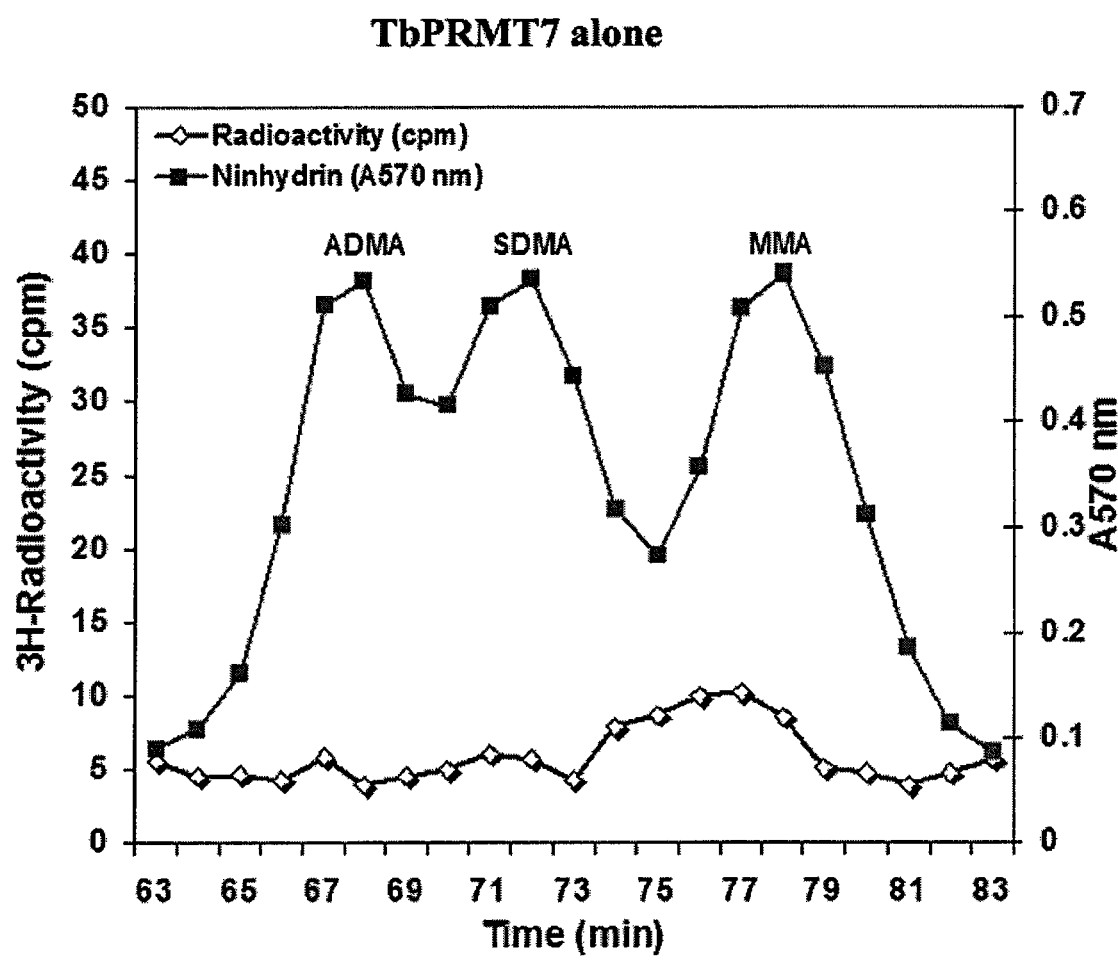
Figure 6E:
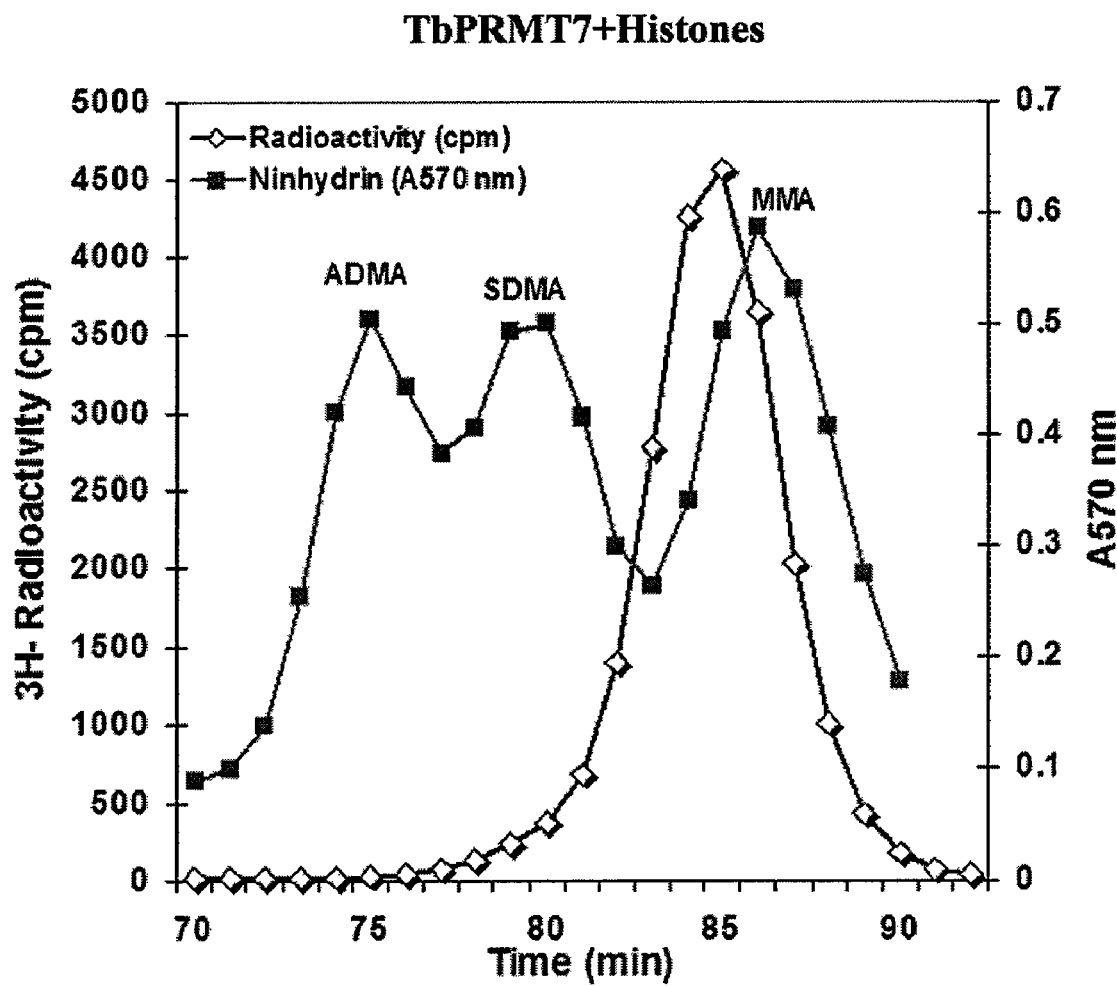
Figure 6F:
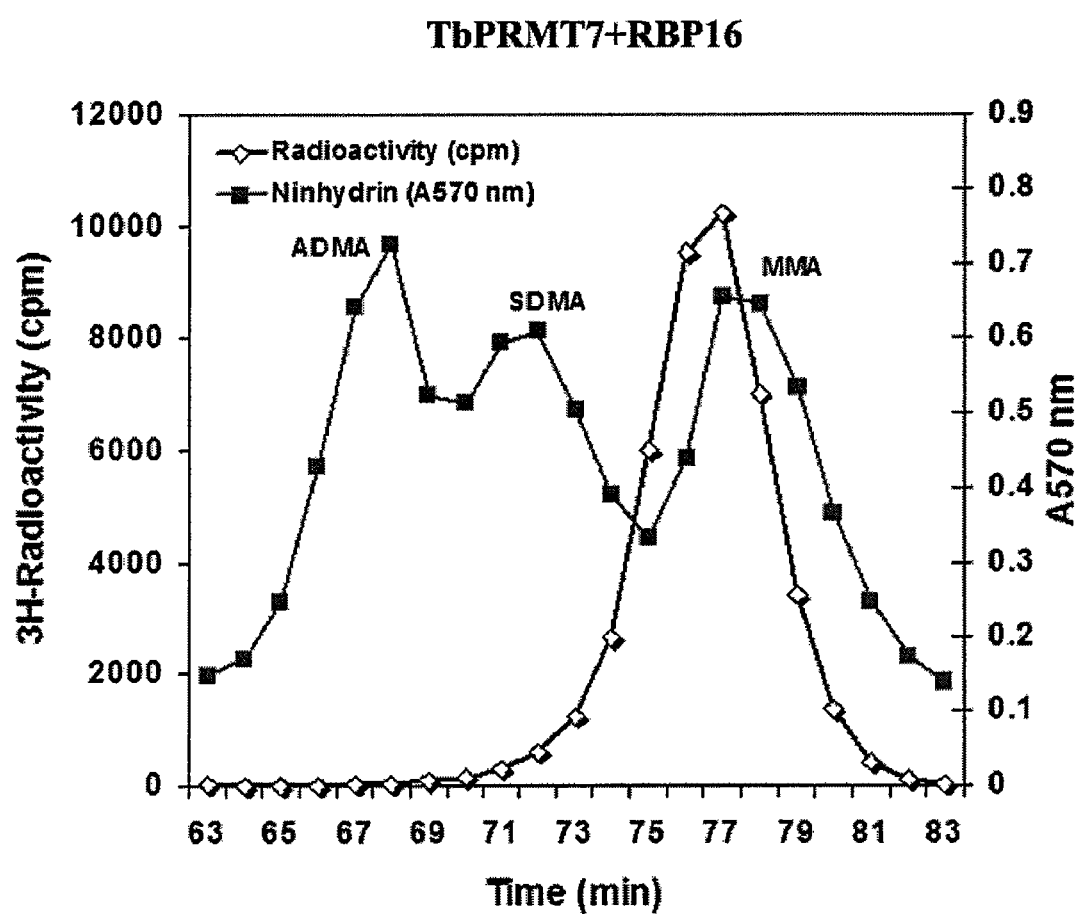

FIG. 5 are test results showing the localization of TbPRMT7 to the cytoplasm. Procyclic form *T. brucei* were transfected with pC-PRMT7-PTP to create a clonal cell line expressing C terminal PTP-tagged TbPRMT7 expressed from one endogenous allele. Cells were fractionated into cytoplasmic and nuclear fractions and the equivalent of $5 \times 10^5$ cells was analyzed with anti-Prot C antibodies, which recognize the PTP tag. Hsp70 and the CTD of RNA polymerase II were used as cytoplasmic and nuclear markers, respectively. WCL, whole cell lysate.

FIG. 6 is a graph showing methylation of RBP16 by TbPRMT7. HPLC analysis of RBP16 protein that was methylated in vitro by TbPRMT7, showing the synthesis of only monomethylarginine (thus, defining TbPRMT7 as a Type III PRMT). HPLC analysis showing no automethylation of enzyme alone (A), and only monomethylarginine produced with either histone (B) or RBP16 (C) substrate. FIG. 6 also shows the methylation of bovine histones by TbPRMT7. FIG. 6 shows that the enzyme produces only MMA on two different substrates. FIG. 6 shows high resolution ion exchange chromatography analysis of methylarginine derivatives catalyzed by TbPRMT7. (A) Three micrograms of GST-Tb-PRMT7 in the absence of additional substrate, was incubated in the presence of $^3$H-AdoMet in PBS for fourteen hours at 22° C. Protein was precipitated with 50% trichloroacetic acid and digested into amino acids by acid hydrolysis. Amino acids were analyzed by cation exchange chromatography in the presence of unlabeled ADMA, SDMA, and MMA standards. 200 µl of each fraction (⅕ of the total fraction) was removed for radioactivity analysis and 100 µL was removed for ninhydrin analysis, and the fractions were counted three times for three minutes each. (B), Ten micrograms of bovine histones were incubated with three micrograms of GST-Tb-PRMT7 in the presence of $^3$H-AdoMet as in A, and reactions were analyzed as in A. (C), Three micrograms of RBP16 were incubated with three micrograms of GST-TbPRMT7 in the presence of $^3$H-AdoMet as in A, and reactions were analyzed as in (A). (D, E, F) In vitro reactions were carried out as in A, B, and C using three micrograms of TbPRMT7 that was treated with thrombin to remove the GST tag.

Figure 7:
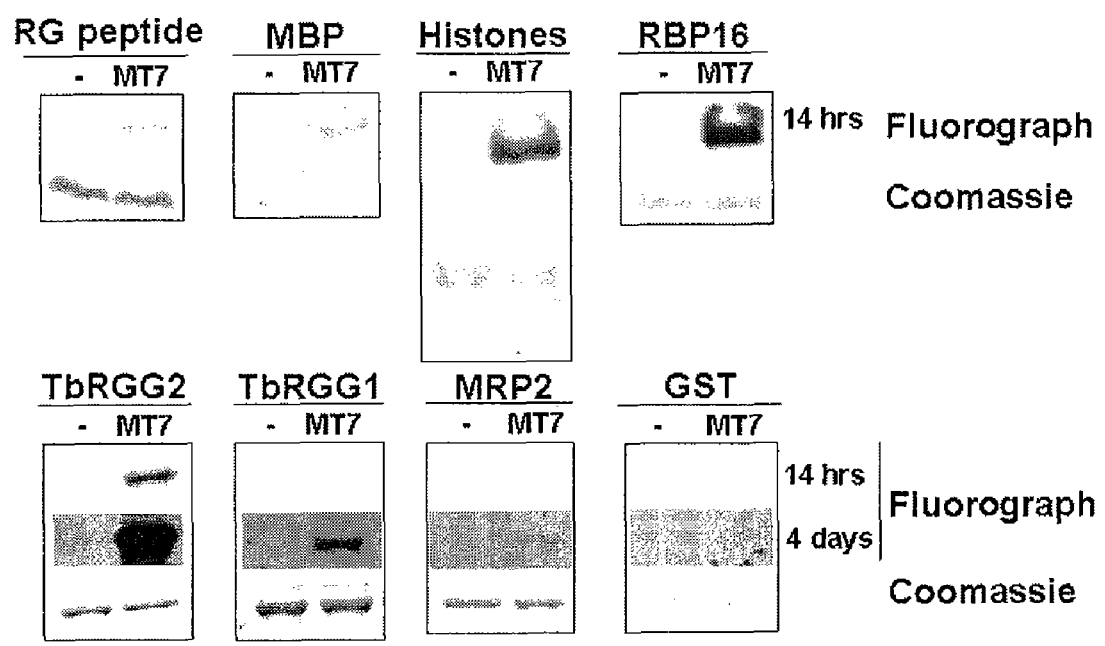

FIG. 7 shows results of reactions with protein or peptide substrates incubated with recombinant TbPRMT7 and 3H-Adomet. Reactions were resolved on SDS-PAGE and stained with Coomassie (to reveal protein) or subjected to fluorography (to reveal methylated substrate). Of the eight substrates tested, only GST was not methylated.

Figure 8:
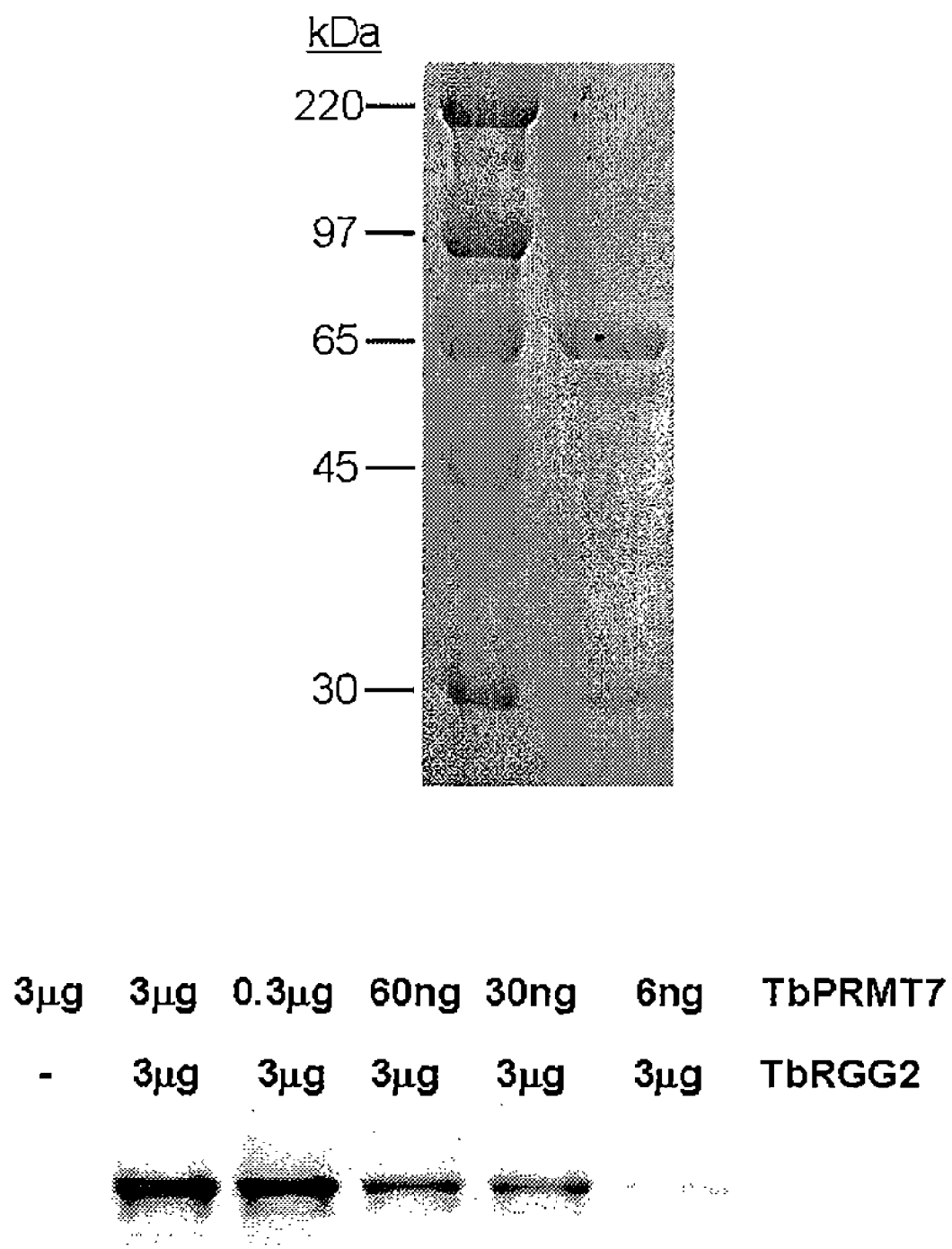

FIG. 8 is an enzyme titration that shows recombinant is active at very low levels. The substrate and enzyme are about the same molecular mass. The faint signal in the no substrate lane (left) is the enzyme binding 'H-AdoMet in a manner stable to SDS-PAGE.

FIG. 9 provides the coding sequence (SEQ ID NO: 6) for the methyltransferase of the present invention. The amino acid sequence (SEQ ID NO:5) is provided below.

FIG. 10 shows TbPRMT7 forms a dimer in vitro and is present in higher order complexes in vivo. A, Anti-Prot C western blot analysis of cytoplasmic extracts from cells expressing TbPRMT7-PTP (equivalent of $5 \times 10^5$ cells) and parental 29-13 cells under denaturing conditions (10% SDS-PAGE). B, Western blot analysis of TbPRMT7-PTP cells, parental 29-13 cells, and 1 µg of recombinant TbPRMT7-His under nondenaturing conditions (4-20% PAGE). C, Cytoplasmic extracts from TbPRMT7-PTP expressing cells were fractionated on a 5-20% glycerol gradient, and the positions of TbPRMT7-PTP revealed by anti-Prot C western blot analysis. The peak position of size markers separated on a parallel gradient are indicated above by arrows.

FIG. 11 shows endogenously tagged TbPRMT7 exhibits type III PRMT activity. A, Endogenously tagged TbPRMT7 has in vitro activity comparable to recombinant GST-TbPRMT7. Right panel; The indicated substrates were incubated with 100 ng of purified TbPRMT7-ProtC from *T. brucei* incubated with either PBS buffer alone (−), 3 µg RBP16, or 10 µg bovine histone in the presence of 2 µCi $^3$H-AdoMet in PBS overnight at room temperature. Left panel; Three micrograms of GST-PRMT7 was used as a positive control with each substrate for activity in vitro. For each reaction the Coomassie stain of the substrate is shown below the resultant fluorograph of activity. B, Purified TbPRMT7-ProtC from *T. brucei* still exhibits Type III PRMT activity. The reactions from A were subjected to high resolution cation exchange chromatography as in FIG. 6.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Nucleic acid sequence" as used herein refers to an oligonucleotide, nucleotide or polynucleotide, and fragments or portions thereof, and to DNA or RNA of genomic or synthetic origin that may be either single- or double-stranded, and represent the sense or antisense strand.

"Amino acid sequence" as used herein refers to peptide or protein sequence.

"TbPRMT7-ProtC" as used herein refers to the protein TbPRMT7 with a C-terminal Protein C tag.

"TbPRMT7-PTP" as used herein refers to the protein TbPRMT7 with an integrated tandem purification PTP tag.

The term "recombinant DNA vector" as used herein refers to DNA sequences containing a desired coding sequence and appropriate DNA sequences necessary for the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenylation signals and enhancers.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species).

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "host cell" refers to any cell capable of replicating and/or transcribing and/or translating a gene, including a heterologous gene.

DESCRIPTION OF THE INVENTION

This disclosure provides a new member of the PRMT Type III class, PRMT7, from the parasite *Trypanosoma brucei*. Recombinant protein has been successfully prepared. The protein disclosed herein methylates at a rate at least 100× higher than Type I and Type II enzymes, and monomethylates a wide range of substrates. PRMT7 can be used as research tool to test the effect on monomethylation on a protein's activity, protein-protein interactions, and/or protein nucleic acid interactions. In addition, production of the enzyme in heterologous mammalian expression systems may prove useful in determining the role of monomethylarginine modification in mammalian cells We utilized a bioinformatic search with human protein arginine methyltransferases to identify homologous enzymes in *Trypanosoma brucei*. Extensive sequence analysis predicted that the identified open reading frame encoded an enzyme with protein arginine methyltransferase activity. Primers corresponding to the extreme 5' and 3' ends of the open reading frame of this enzyme were designed, with a BamHI restriction site on the 5' primer and an XhoI site on the 3' primer. (The 5' primer was PRMT7-5 (SEQ ID NO: 1): 5'-GCGAATTCATGAAGCGCACACCTGTTAG-3' and the 3' primer was PRMT7-3 (SEQ ID NO: 2):5'-GGAAGCTTTTCCTTCTGACTGGCATC-3'.) The primers were used to amplify oligo-dT primed cDNA from procyclic form *T. brucei*. The resulting product was ligated into pCR2.1 to give pCR-TbPRMT, and pCR-TbPRMT was transformed into *Escherichia coli*. The insert containing the open reading frame was released from pCR-TbPRMT by digestion with BamHI and XhoI and ligated into the BamHI and XhoI sites of pGEX-4T1 to give pGEX-TbPRMT. *E. coli* harboring pGEX-TbPRMT were induced with IPTG for 3 hours at 37 degrees C. for production of the enzyme as a recombinant fusion protein with an N-terminal glutathione-S-transferase tag. The resulting GST fusion protein was purified by affinity chromatography on glutathione agarose. Enzyme activity was assayed in phosphate buffered saline using 6 ng-3 ug enzyme, 3 ug of mixed bovine histones (Sigma), and 0.2 uM (1 uCi) of 3H-S-adenosyl methionine. Histones were resolved by SDS-PAGE and methylated proteins identified by fluorography. This assay demonstrated that the recombinant enzyme possesses protein arginine methyltransferase activity and utilizes histone H3 as a substrate. The nature of the methyl groups added to the protein (in the above reaction) was determined by HPLC of trypsin digested protein compared to known standards for monomethyl-arginine (MMA), asymmetric dimethylarginine (ADMA), and symmetric dimethylarginine (SDMA) (FIG. 6). The production of solely MMA defines a protein arginine methyltransferase as Type III.

For integration of the tandem purification PTP tag (Schimanski, B., Nguyen, T. N., and Gunzl, A. (2005) Eukaryotic Cell 4(11), 1942-1950) into the endogenous TbPRMT7 locus, primers PRMT7-5'-ApaI (SEQ ID NO: 3): (5'-GT GGGCCCGCTATTCAGAGTCGACTTTAGC-3') and PRMT7-3'-NotI (SEQ ID NO: 4): (5'-CA GCGGCCGCGTTGTTTTGCCCTCGC-3', encompassing nucleotides 830 to 1170 of the TbPRMT7 open reading frame and introducing ApaI and NotI restriction sites, were used to amplify the 3' end of TbPRMT7 and introduce it into the ApaI-NotI restriction sites of pC-PTP (Schimanski, B., Nguyen, T. N., and Gunzl, A. (2005) Eukaryotic Cell 4(11), 1942-1950), which we modified to contain the puromycin resistance gene. pC-PRMT7-PTP was linearized using the unique HpaI restriction site within TbPRMT7 and transfected into 29-13 PF *T. brucei* cells. Transgenic cells were selected with 1 μg/mL puromycin and cloned by limiting dilution. TbPRMT7-PTP expression was verified by Western blotting against the protein C tag within PTP, which detected only the expected band at 63 kDa.

Figure 11A:
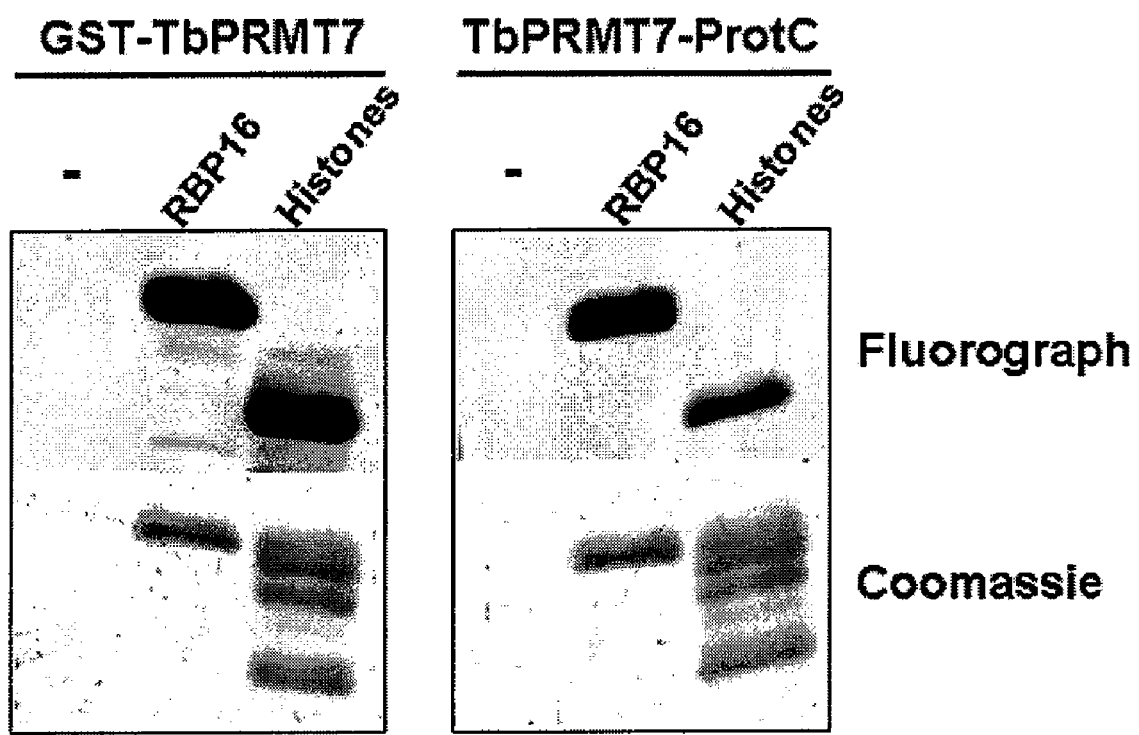
Figure 11B:
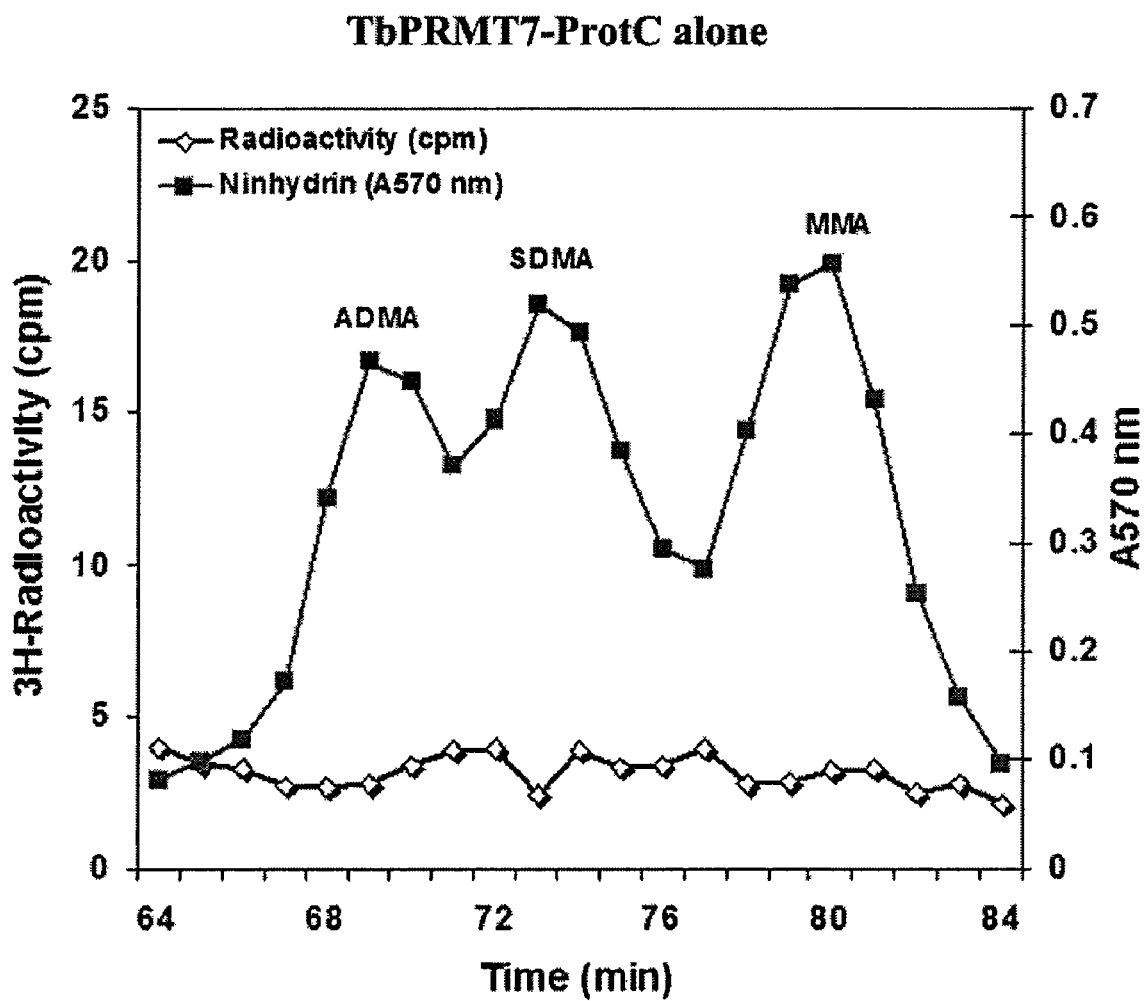
Figure 11B:
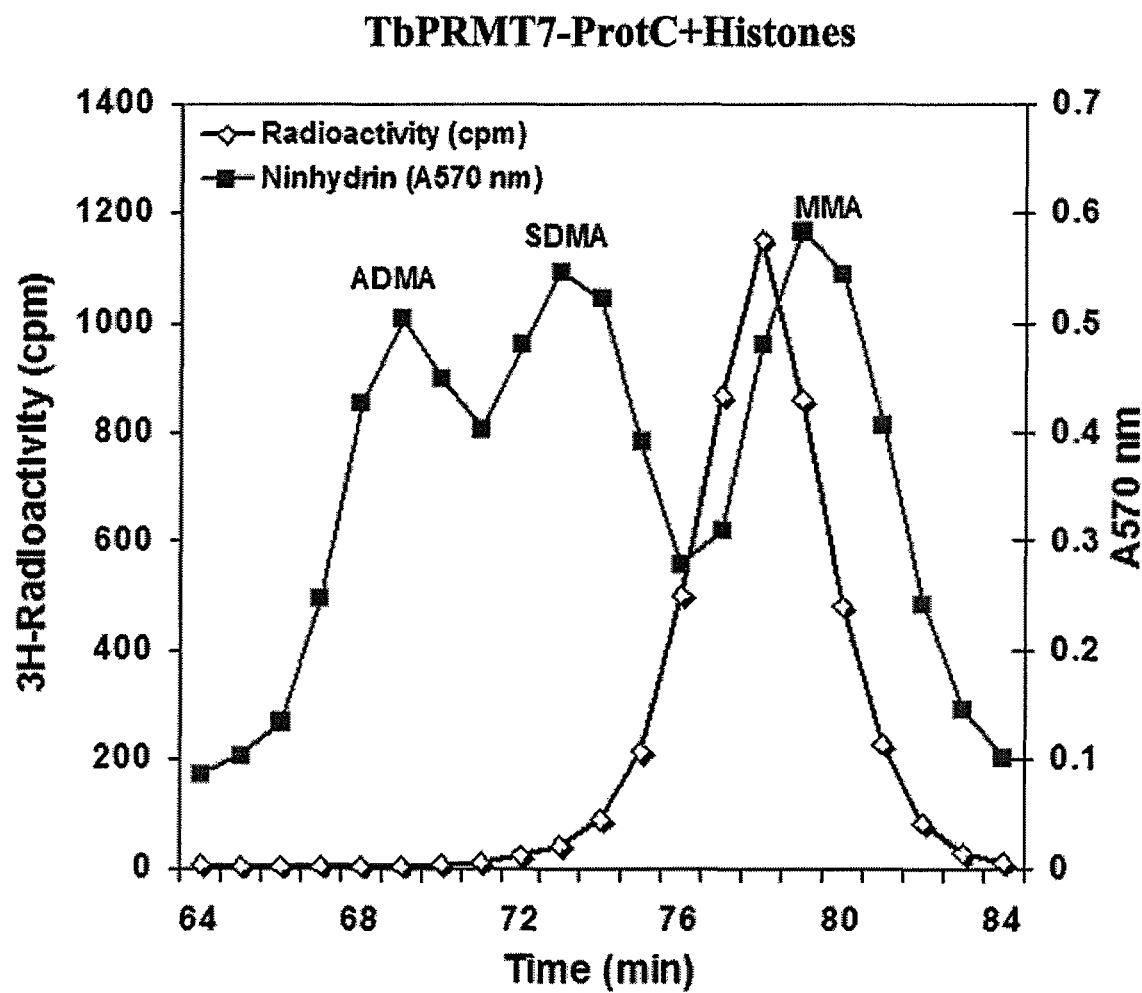
Figure 11B:
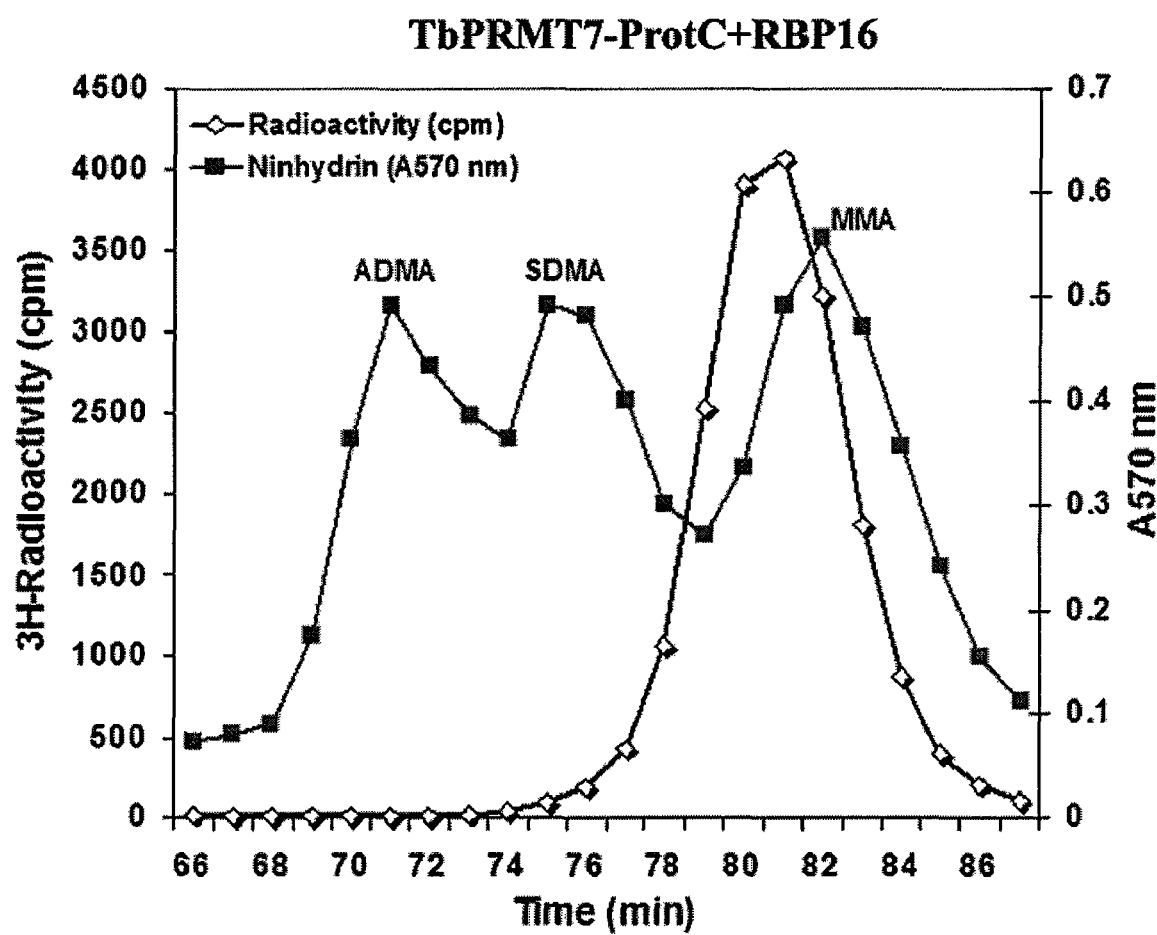

The association of TbPRMT7 with in vivo binding partners could change its Type III activity. To determine whether TbPRMT7 purified from *T. brucei* retains Type III activity, we purified TbPRMT7-PTP from PF cytoplasmic extracts using the tandem affinity purification method (Schimanski, B., Nguyen, T. N., and Gunzl, A. (2005) Eukaryotic Cell 4(11), 1942-1950), resulting in TbPRMT7 with a C-terminal Protein C tag (TbPRMT7-ProtC). The enzymatic activity of TbPRMT7-ProtC was determined in vitro either in the absence of substrate and either bovine histones or trypanosomal RBP16 as substrates. Recombinant GST-TbPRMT7 was used as a positive control (FIG. 11A). TbPRMT7-ProtC strongly methylated both histones and RBP16, demonstrating that the in vivo C-terminally tagged enzyme is active. The reactions shown in FIG. 11A were also subjected to high resolution cation exchange chromatography to determine whether the TbPRMT7-ProtC exhibited Type III methyltransferase activity as did the recombinant TbPRMT7. As shown in FIG. 11B, TbPRMT7-ProtC did not appreciably methylate itself (FIG. 11B). Moreover, the enzyme purified from *T. brucei* exhibited solely Type III PRMT activity towards both histones and RBP16 (FIG. 11B), with no appreciable SDMA or ADMA formed. These results confirm that the highly active TbPRMT7 catalyzes only Type III PRMT activity on all substrates analyzed, regardless if the enzyme is recombinant or purified from the parasite.

Amino acid sequence of the enzyme of the present disclosure (SEQ ID NO: 5): *T. brucei* Gene DB identifier: >Tb927.7.5490 |||arginine N-methyltransferase, putative|*Trypanosoma brucei*|chr 7|||Manual

```
MPPKQHRHQK KDKNDNALQN TIGFVPPGAT LASVSGYRPP

DAFVNRIDRN IPVPARLRHT PVSLIEAVND FHYAMMNDEE

RNNFYYEVLK KHVTPETGVL EIGAGSGLLS LMAAKLGAKW

VVAVEGSEEL AKLARENIRA NNMEHQVKVL HMMSTELKSK

HLPEPPDVLL SEIFGTMMLG ESALDYVVDV RNRLLKPTTK

IIPQFGTQYA VPIECDALHR ISSVSGWRDL DLKHMMTLQD

TVSIVFAKHY GIRMNSVNFR RLSDPIELFR VDFSSSNRND

IPRRKHFDVV AKESGTAHAM LFYWKVTDDE FVMSTDPEDT

VNNFPRDMQW GQALQLLDAS NGPLPTPVVF TEGKNYNFEC

NFSGDRVILH MQLCPESGNG EMTECEGKTT
```

TbPRMT7 has shown that it methylates the majority of substrates tested. TbPRMT7 was incubated with two in vitro substrates: RBP16 and Bovine Histones. Results indicate methylation occurred.

Protein arginine methyltransferases (PRMTs) catalyze the transfer of methyl groups(s) from AdoMet (S-adenosyl methionine) to terminal nitrogen of arginine. PRMTs are involved in RNA processing, signal transduction, DNA repair and transcription regulation. PRMTs remain associated with the substrates and can allow the identification of the substrates and co-factors and complexes.

It is not intended that the present invention be limited by the manner in which the methyltransferase is used. Research laboratories studying the burgeoning field of protein arginine methylation could use this reagent to study the role of monomethylation on protein-protein and protein-nucleic acid interactions, and as negative control in experiments addressing the role of dimethylation. The enzyme of the present disclosure is the most active recombinant type III protein arginine methyltransferase described to date. It is a unique, highly active recombinant arginine methyltransferase capable of monomethylation of peptides and proteins. It should be valuable for in vitro assays with many different methylated proteins, permitting, for example, comparing interactions with specific proteins or nucleic acids with unmethylated vs. monomethylated vs. dimethylated versions. In one embodiment, the present invention contemplates assaying activities of such proteins, including but not limited to, determining potential RNA helicases or ATPases.

The invention claimed is:

1. A purified methyltransferase having the amino acid sequence of SEQ ID NO:5.

2. The purified methyltransferase of claim 1 mixed with substrate.

3. A nucleic acid sequence coding for the methyltransferase of claim 1.

4. A vector comprising the nucleic acid sequence of claim 3.

5. The vector of claim 4, wherein the nucleic acid sequence is operably linked to a heterologous promoter.

6. A host cell comprising the vector of claim 4.

* * * * *

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: synthetic

<400> SEQUENCE: 1
gcgaattcat gaagcgcaca cctgttag                                      28

<210> SEQ ID NO 2
<211> LENGTH: 26
<212> TYPE: DNA
<213> ORGANISM: Artificial Sequence
<220> FEATURE:
<223> OTHER INFORMATION: synthetic

<400> SEQUENCE: 2
ggaagctttt ccttctgact ggcatc                                        26

<210> SEQ ID NO 3
<211> LENGTH: 30
<212> TYPE: DNA
<213> ORGANISM: Artificial Sequence
<220> FEATURE:
<223> OTHER INFORMATION: synthetic

<400> SEQUENCE: 3
gtgggcccgc tattcagagt cgactttagc                                    30

<210> SEQ ID NO 4
<211> LENGTH: 26
<212> TYPE: DNA
<213> ORGANISM: Artificial Sequence
<220> FEATURE:
<223> OTHER INFORMATION: synthetic

<400> SEQUENCE: 4
cagcggccgc gttgttttgc cctcgc                                        26

<210> SEQ ID NO 5
<211> LENGTH: 390
<212> TYPE: PRT
<213> ORGANISM: Trypanosoma brucei

<400> SEQUENCE: 5

Met Pro Pro Lys Gln His Arg His Gln Lys Lys Asp Lys Asn Asp Asn
1               5                   10                  15
```

Ala Leu Gln Asn Thr Ile Gly Phe Val Pro Pro Gly Ala Thr Leu Ala
            20                  25                  30

Ser Val Ser Gly Tyr Arg Pro Pro Asp Ala Phe Val Asn Arg Ile Asp
         35                  40                  45

Arg Asn Ile Pro Val Pro Ala Arg Leu Arg His Thr Pro Val Ser Leu
 50                  55                  60

Ile Glu Ala Val Asn Asp Phe His Tyr Ala Met Met Asn Asp Glu Glu
 65                  70                  75                  80

Arg Asn Asn Phe Tyr Tyr Glu Val Leu Lys Lys His Val Thr Pro Glu
                 85                  90                  95

Thr Gly Val Leu Glu Ile Gly Ala Gly Ser Gly Leu Leu Ser Leu Met
            100                 105                 110

Ala Ala Lys Leu Gly Ala Lys Trp Val Val Ala Val Glu Gly Ser Glu
        115                 120                 125

Glu Leu Ala Lys Leu Ala Arg Glu Asn Ile Arg Ala Asn Asn Met Glu
130                 135                 140

His Gln Val Lys Val Leu His Met Met Ser Thr Glu Leu Lys Ser Lys
145                 150                 155                 160

His Leu Pro Glu Pro Pro Asp Val Leu Leu Ser Glu Ile Phe Gly Thr
                165                 170                 175

Met Met Leu Gly Glu Ser Ala Leu Asp Tyr Val Val Asp Val Arg Asn
            180                 185                 190

Arg Leu Leu Lys Pro Thr Thr Lys Ile Ile Pro Gln Phe Gly Thr Gln
        195                 200                 205

Tyr Ala Val Pro Ile Glu Cys Asp Ala Leu His Arg Ile Ser Ser Val
210                 215                 220

Ser Gly Trp Arg Asp Leu Asp Leu Lys His Met Met Thr Leu Gln Asp
225                 230                 235                 240

Thr Val Ser Ile Val Phe Ala Lys His Tyr Gly Ile Arg Met Asn Ser
                245                 250                 255

Val Asn Phe Arg Arg Leu Ser Asp Pro Ile Glu Leu Phe Arg Val Asp
            260                 265                 270

Phe Ser Ser Asn Arg Asn Asp Ile Pro Arg Arg Lys His Phe Asp
        275                 280                 285

Val Val Ala Lys Glu Ser Gly Thr Ala His Ala Met Leu Phe Tyr Trp
290                 295                 300

Lys Val Thr Asp Asp Glu Phe Val Met Ser Thr Asp Pro Glu Asp Thr
305                 310                 315                 320

Val Asn Asn Phe Pro Arg Asp Met Gln Trp Gly Gln Ala Leu Gln Leu
                325                 330                 335

Leu Asp Ala Ser Asn Gly Pro Leu Pro Thr Pro Val Val Phe Thr Glu
            340                 345                 350

Gly Lys Asn Tyr Asn Phe Glu Cys Asn Phe Ser Gly Asp Arg Val Ile
        355                 360                 365

Leu His Met Gln Leu Cys Pro Glu Ser Gly Asn Gly Glu Met Thr Glu
370                 375                 380

Cys Glu Gly Lys Thr Thr
385                 390

<210> SEQ ID NO 6
<211> LENGTH: 1173
<212> TYPE: DNA
<213> ORGANISM: Trypanosoma brucei

<400> SEQUENCE: 6

-continued

```
atgcccccaa agcagcaccg ccaccaaaag aaggacaaga acgacaatgc gttgcagaac    60
acaattgggt ttgttcctcc tggagccact ctcgctagtg tgtccggtta ccgtcctcct   120
gacgcctttg ttaaccgaat cgatagaaat ataccggtcc ccgcccgcct gcgccacaca   180
ccagtttccc tcattgaagc ggtgaatgat ttccactacg caatgatgaa tgatgaggaa   240
cgcaataatt tctactatga ggttttgaag aaacatgtga ctccagaaac tggtgtactg   300
gagattggtg ctggatcagg tttactgtct ctcatggccg ctaagcttgg tgcgaagtgg   360
gttgttgcag tggagggaag cgaagaattg gcgaagttgg cacgtgagaa catccgtgct   420
aataatatgg aacatcaggt aaaggttctt catatgatga gtacagagct caaatcaaag   480
cacttacccg aaccaccgga tgttcttttg tcggagatat ttggaacgat gatgcttgga   540
gagtcggcac tagattatgt tgtggatgtg agaaataggt tactgaagcc aacaacgaaa   600
ataattccac agtttggaac gcaatacgcc gtccccatcg agtgcgacgc tcttcaccgt   660
atttcatctg tatcgggctg gcgtgacttg gacctgaagc atatgatgac attgcaggat   720
accgtgagta ttgtctttgc taaacactac ggtatccgta tgaacagtgt gaacttcagg   780
aggttaagcg atcccataga gctattcaga gtcgacttta gctcctcgaa tcggaacgat   840
attcctcggc gaaagcactt cgacgttgtg gctaaagaga gtggaacggc ccatgcaatg   900
ttgttctact ggaaagttac cgacgatgaa tttgtcatgt caacggaccc ggaagacaca   960
gtcaacaact tcccacgtga tatgcagtgg ggtcaggcgc ttcagctgtt ggacgcctct  1020
aacggccctc tgcccacacc ggttgtattc accgagggaa agaattataa ctttgagtgt  1080
aattttccgg gagaccgcgt gattcttcac atgcagctct gccccgaaag tgggaacggt  1140
gaaatgactg agtgcgaggg caaaacaacc tga                               1173
```